United States Patent [19]

Swim et al.

[11] Patent Number: Plant 5,295

[45] Date of Patent: Oct. 16, 1984

[54] ROSE PLANT CV. 'ARONANCE'

[75] Inventors: Herbert C. Swim; Jack E. Christensen, both of Ontario, Calif.

[73] Assignee: Armstrong Nurseries, Inc., Ontario, Calif.

[21] Appl. No.: 413,497

[22] Filed: Aug. 31, 1982

[51] Int. Cl.[3] ..... A01H 5/00

[52] U.S. Cl. ..... Plt./11

[58] Field of Search ..... Plt./11

[56] References Cited

PUBLICATIONS

Meikle, Catherine E. (Ed) *Modern Roses* 8 published by the McFarland Co., Harrisburg, PA. 1980, pp. 150, 151, 342 and 343 only.

*Primary Examiner*—James R. Feyrer

*Attorney, Agent, or Firm*—Synnestvedt & Lechner

[57] ABSTRACT

A new variety of rose plant of the hybrid tea class, being a half-hardy outdoor tall bush seedling, particularly adapted for garden decoration. This new rose cultivar is unique and distinguishable from existing rose cultivars by the following combination of characteristics: its large flowers of pastel coloration are borne singly on long strong stems suitable for cutting; its abundant large deep green foliage attractively clothes a tall, well-branched bush; its large, long pointed buds open in a classic spiraled form; and its vigor and profusion of bloom provides an easy-to-grow satisfying garden plant.

1 Drawing Figure

1

This invention relates to a new class of hybrid tea rose. The plant is a seedling of the half-hardy, tall, bushy outdoor type, cultivated for garden decoration. It was first propagated in Ontario, Calif. References to the growth and behavior of the plant pertain to plants raised in Southern California.

This new rose cultivar is unique and distinguishable from existing rose cultivars by the following combination of characteristics: its large flowers of pastel coloration are borne singly on long strong stems suitable for cutting; its abundant large deep green foliage attractively clothes a tall, well-branched bush; its large, long pointed buds open in a classic spiraled form; and its vigor and profusion of bloom provides an easy-to-grow satisfying garden plant.

The new variety has as its seed parent "American Heritage" (U.S. Plant Pat. No. 2,687), and, as its pollen parent, "First Prize" (U.S. Plant Pat. No. 2,774). It holds its distinguishing characteristics through succeeding propagations by budding.

This new rose cultivar may be distinguished from its seed Parent, American Heritage, by the following combination of characteristics.

Whereas American Heritage bears flowers with petals of average breadth, the new cultivar bears flowers with significantly broader petals, essentially as described and illustrated herein.

American Heritage bears flowers of average size (4 to 5 inches), whereas the new rose bears significantly larger flowers (5 to 6 inches).

Under Ontario, Calif. growing conditions, the new rose cultivar has an above average resistance to powdery mildew, whereas American Heritage shows a very poor resistance to powdery mildew under the same conditions.

Whereas the new rose cultivar produces a tall, broad, well-branched plant, American Heritage produces a plant of tall columnar habit with significantly less branching.

This new rose cultivar may be distinguished from its pollen parent, First Prize, by the following combination of characteristics.

2

Whereas First Prize bears flowers of a blended pink coloration, the new rose bears flowers of a light yellow coloration tinged with pink essentially as described and illustrated herein.

The new cultivar produces a plant with a tall habit (5 to 6 feet), whereas the bush of First Prize is significantly shorter (3 to 4 feet) under Ontario, Calif. growing conditions.

Whereas the new rose cultivar has an above average resistance to powdery mildew under Ontario, Calif. growing conditions, First Prize is significantly less resistant to powdery mildew.

First Prize is a cultivar of moderate vigor, whereas the new rose is significantly more vigorous.

FLOWER

The new variety usually bears its flowers singly, but sometimes two to three blooms are carried on one stem, in irregular, flat clusters. The stems are strong and long. The plant blooms abundantly outdoors, and nearly continuously during the growing season. It has a slight tea fragrance.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the R.H.S. Colour Chart published by The Royal Horticultural Society of London, England.

BUD

The peduncle is average to long in length and heavy in caliper, being erect, stiff and moderately smooth, with some stipitate glands.

Before the calyx breaks, the bud is large in size, and long, pointed ovoid in form, usually having foliaceous appendages and gladular bloom on the surface of the bud. Usually, the plant has slender foliaceous parts extend beyond the tip of the bud equal to one-fourth or more of its length.

As the calyx breaks, the color is between Yellow, 8C and Yellow, 9C and sometimes is blushed between Red, 44C and Red, 41B. The inner surface of the sepals carries a fine, wooly tomentum. Margins of the sepals are lined with stipitate glands and hairs.

As the first petal opens, the bud is large in size, and long, pointed ovoid in form. The color on the outside of the petal base is near Yellow, 12A and rapidly suffuses to between Yellow, 12C and Yellow-Orange, 18C and is sometimes blushed with between Red, 44C and Red, 41B. The majority of the inside surface of the petal has a coloration essentially the same as the outside petal except blushing is less intense at the petal edge only — usually between Red, 49B and Red, 49A. The bud opens up well, and is not prevented from opening by cold, hot, wet or dry weather.

BLOOM

The bloom when fully open is large in size, ranging from 5 to 6 inches. The petalage is very double, with from 30 to 35 petals, plus from 2 to 5 petaloids arranged regularly. The bloom is high centered and globular at first, becoming open to cupped. At first the petals are somewhat cupped, with tips reflexed outward, and become later at maturity more loosely cupped, with tips reflexed outward.

PETALS

The petals are of medium thickness, with inside slightly satiny and outside slightly shiny. The outside petals are broadly obovate and have a rounded apex. The intermediate petals are round to broadly obovate in shape and have a rounded apex. The inside petals are nearly round to obovate in shape and have a rounded apex. The colors may be modified by being bordered, margined, penciled, blotched, shaded and/or washed or tinted with other colors.

The description immediately following is of a newly opened flower of a plant grown outdoors in the month of June in Ontario, Calif.

The outer surface of the outside petal has a basal coloration between Yellow, 12A and Yellow, 12B and suffuses to between Yellow, 12C and Yellow, 11D with very occasional blushing near the petal edge of near Red, 49B. The inner surface of outside petals shows the same coloration as the outer surface of the outside petal but with more accentuated blushing at the petal edge.

The outer surface of intermediate petals shows the same coloration as the outer surface of outside petals but without any blushing. The inside surface of the intermediate petals shows the same coloration as the inside surface of the outside petal but with much less blushing.

The inside and outside surfaces of the inner petals show a petal base coloration near Yellow, 12A and Yellow, 12B which suffuses to between Yellow, 12C and Yellow-Orange, 14D.

The description which follows was made from a rose that was open for three days. It had been grown outdoors in the month of June, at Ontario, Calif.

The outer surface of the inside and outside petals has a basal coloration near Yellow, 12D which suffuses to between Yellow, 11D and Yellow, 8D. The inside surface of the inside petals is of the same coloration as the outer surface of the inside and outside petals. The inside surface of the outside petal was the same coloration as the outer surface, but blushes near the petal edge to between Red 49B and Red, 49D.

The general color effect of the newly opened flower is between Yellow, 12C and Yellow, 11D, deepening toward the center to between Yellow, 12C and Yellow-Orange, 14D. The outside petal edges are blushed with near Red, 49B. The bloom after being three days open, gives a general color effect of between Yellow, 11D and Yellow, 8D. The outside petal edges are blushed with between Red, 49B and Red, 49D. The petals drop off cleanly. They are not particularly affected by cold, hot, wet or dry weather.

The flowers on the bush in the garden persist from three to five days in the month of June. Cut roses grown outdoors and kept at living-room temperatures will last from four to five days in the month of June.

REPRODUCTIVE ORGANS

There are many stamens which are arranged regularly about the pistils and a few are mixed with petaloids.

Filaments are medium-length to long and most are with anthers.

The anthers are of medium size and open at various times. The color when immature is near Yellow-Orange, 15A and when mature is near Brown, 200C.

Pollen is abundant and near Yellow-Orange, 15D in color.

There are many (approximately 130) pistils.

The styles are moderately uneven, of short to average length, average to heavy in caliper, and somewhat bunched.

The stigma is near Yellow-Orange, 15B.

Most of the ovaries are enclosed in the calyx.

The hips are of average to long length, ovoid in shape and with very smooth, fleshy walls. When immature, they are near Yellow-Green, 144B in color.

The sepals are permanent, medium-length and spear-shaped. The color on the inside is between Yellow-Green, 147D and Yellow-Green, 148D. The outside is near Yellow-Green, 146B in color.

There is an average number (from 6 to 5 of medium to large seeds.

FOLIAGE

The compound leaves usually comprise from three to five leaflets. They are abundant in quantity, large and heavy in size and somewhat leathery and semi-glossy in texture. The leaflets are oval, with acute apex and a round base. The margin is doubly serrate.

The upper surface of the mature foliage is between Yellow-Green, 147A and Green, 136A in color. The under surface is a color between Greyed-Green, 191A and Green, 138B.

The young foliage has an upper surface which is between Greyed-Purple, 187A and Greyed-Purple, 187B in color. The under surface is between Red-Purple, 59B and Greyed-Purple, 187B.

The rachis is average to heavy in size, the upper side being grooved and with a few stipitate glands on the edges. The underside is sparsely prickly.

The stipules are medium-length to long, moderately narrow, with medium-length points turning out at an angle of more than 45°.

The plant displays a more than average resistance to mildew and blackspot when compared to other varieties grown under comparable conditions in the same locality.

GROWTH

The plant is of bushy, upright habit, and is much branched. Its growth is very vigorous. The canes are medium to heavy in caliper.

The main stems are between Yellow-Green, 146B and Yellow-Green, 148A in color. They bear several large prickles which are of a medium-length, almost straight to hooked slightly downward, with a short moderately long, broad base. The color is near Grey-Brown, 199D. There are no small prickles and no hairs.

The branches are between Yellow-Green, 147A and Yellow-Green, 148A in color and sides exposed to sunlight blush to near Greyed-Purple, 187B. They bear several large prickles which are of medium-length, almost straight to hooked slightly downward and have a moderately long, broad base. The color is near Greyed-Red, 178B. There are a few small prickles near Greyed-Red, 178B in color and no hairs.

New shoots have a color between Greyed-Purple, 183B and Greyed-Purple, 187B, are of medium-length, almost straight to hooked slightly downward and with a short moderately long, broad base. There are several small prickles and a few hairs both near Greyed-Purple, 187B in color.

We claim:

1. A new and distinct variety of rose plant of the hybrid tea class, substantially as herein shown and described, being particularly characterized in that its large pastel hued flowers are borne singly on long, strong stems, its tall, well-branched bushy habit and large deep green foliage, its large, long pointed buds that open in a classic spiral form and its vigor and profusion of bloom.

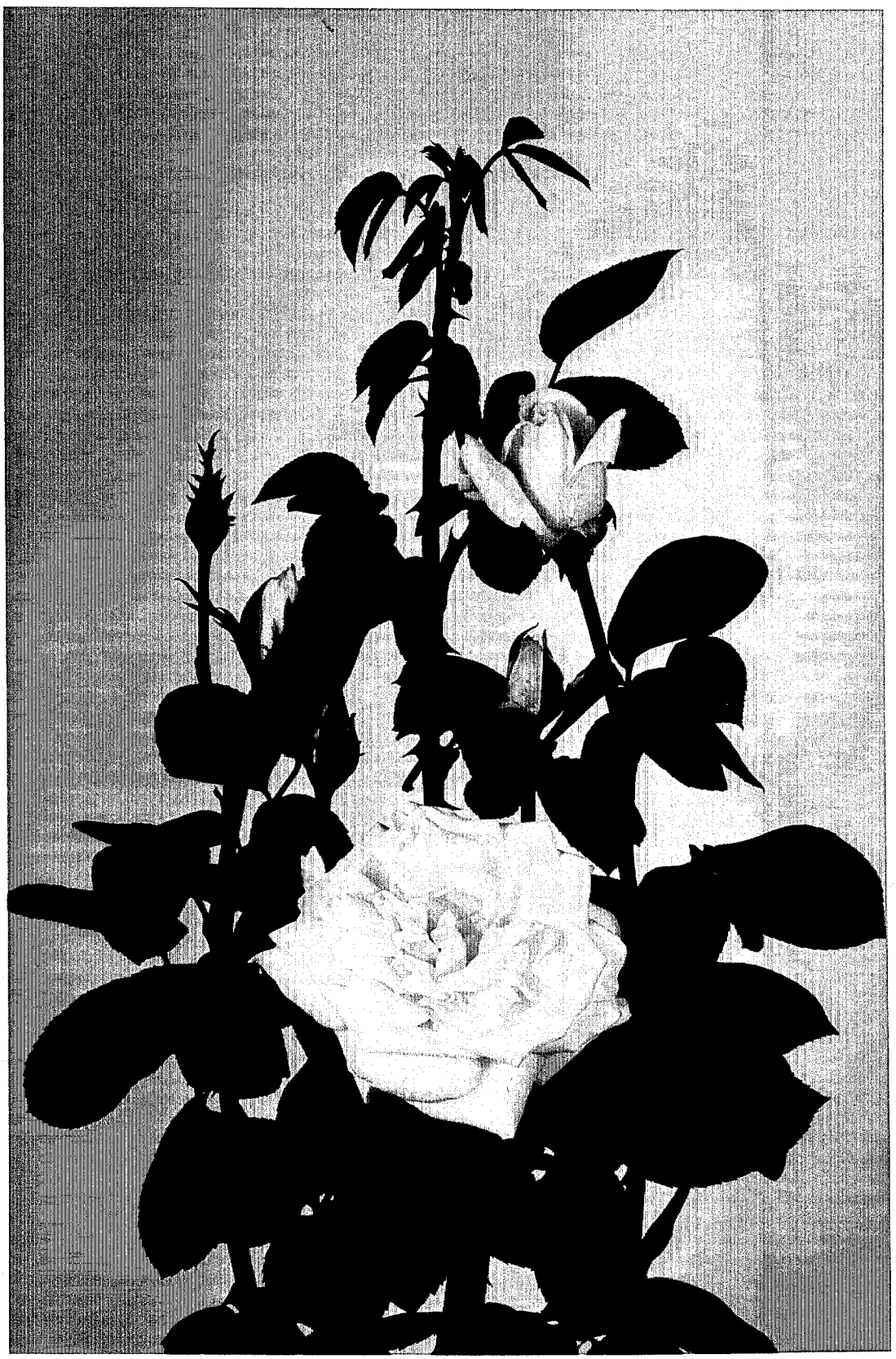

* * * * *